United States Patent
Lopez et al.

(10) Patent No.: US 7,637,484 B2
(45) Date of Patent: Dec. 29, 2009

(54) STEAM INJECTORS

(75) Inventors: Franck Lopez, Saint Macaire en Mauges (FR); Roland Ringström, Veberöd (SE)

(73) Assignee: Tetra Laval Holding & Finance SA, Pully (CH)

( * ) Notice: Subject to any disclaimer, the term of this patent is extended or adjusted under 35 U.S.C. 154(b) by 539 days.

(21) Appl. No.: 10/546,735

(22) PCT Filed: Feb. 27, 2004

(86) PCT No.: PCT/SE2004/000270

§ 371 (c)(1),
(2), (4) Date: Jun. 15, 2006

(87) PCT Pub. No.: WO2004/075670

PCT Pub. Date: Sep. 10, 2004

(65) Prior Publication Data

US 2006/0237859 A1    Oct. 26, 2006

(30) Foreign Application Priority Data

Feb. 27, 2003   (SE) ...................... 0300513

(51) Int. Cl.
*B01F 3/04*   (2006.01)
(52) U.S. Cl. .................. 261/76; 261/DIG. 10
(58) Field of Classification Search ............. 261/76, 261/DIG. 10, DIG. 76
See application file for complete search history.

(56) References Cited

U.S. PATENT DOCUMENTS

| 3,219,483 | A | * | 11/1965 | Goos et al. ................ 127/28 |
| 3,981,946 | A | * | 9/1976 | Soya et al. ................ 261/64.3 |
| 3,984,504 | A | | 10/1976 | Pick |
| 4,160,002 | A | * | 7/1979 | Janovtchik ................ 261/76 |
| 4,689,237 | A | * | 8/1987 | Fabre ................ 426/521 |
| 4,931,225 | A | | 6/1990 | Cheng |
| 5,863,587 | A | * | 1/1999 | Badertscher et al. ....... 426/511 |
| 6,082,712 | A | | 7/2000 | Cincotta et al. |
| 6,082,713 | A | * | 7/2000 | King ................ 261/79.2 |
| 6,361,025 | B1 | * | 3/2002 | Cincotta et al. ............ 261/77 |
| 7,048,958 | B2 | * | 5/2006 | de Jong et al. ............ 426/511 |

* cited by examiner

*Primary Examiner*—Scott Bushey
(74) *Attorney, Agent, or Firm*—Buchanan Ingersoll & Rooney PC

(57) ABSTRACT

The invention relates to a method and a device in a steam injector. The steam injector is of the type which includes an injector housing with an inlet for steam and an inlet for the product which is to be treated. In the injector housing there is also an outlet for the ready-treated product. In the injector the steam is brought together with the product. The device includes a throttle washer which is placed immediately after the product outlet. The throttle washer entails that the pressure is raised immediately before the product leaves the injector. The pressure increase entails an improved steam distribution in the product and that the risk of sedimentation in the product is counteracted. The device also entails that disturbing noise that may occur in the injector is considerably reduced.

8 Claims, 1 Drawing Sheet

STEAM INJECTORS

This application is a U.S. national stage application based on International Application No. PCT/SE/2004/000270 filed on Feb. 27, 2004, and claims priority under 35 USC § 119(a) to Swedish Application No. 0300513-9 filed on Feb. 27, 2003.

TECHNICAL FIELD

The present invention relates to a method of improving the steam distribution in a steam injector of the type, which has an inlet for steam, an inlet for product which is to be treated and where the steam is brought together with the product, the injector also having an outlet for the ready-treated product.

The present invention also relates to a device in a steam injector, the steam injector being of the type which comprises an injector housing with an inlet for steam, as well as an inlet for product and where the steam is brought together with the product, the injector also having an outlet for the product.

BACKGROUND ART

As regards the heat treatment of liquid or pumpable foods, use may be made of steam in order quickly and efficiently to heat up the food product. One of the methods in existence for introducing steam directly into a product is to employ an injector.

Depending on the temperature to which it is intended to heat the product, it is possible to obtain a pasteurised or an aseptic product, or alternatively a product possessing extended shelf-life in cold storage. Such products may be dairy produce, juices, viscous food products or the like. The commonest method is to heat the product to a temperature where there is a total destruction of harmful micro-organisms. This gives a food product which maintains stability on storage at room temperature. No unbroken refrigeration chain for storage is necessary, which may be an advantage above all in the developing countries.

Direct heating of the product, by introducing steam into the product, gives a rapid and efficient heating. As a result of the rapid method, it is possible to reduce treatment time, which in total gives a reduced thermal effect on the product and a product will be obtained which maintains higher quality, above all as regards flavour.

There is a large number of injectors on the market which all are of similar design and construction, with an inlet for the product which is to be treated and an outlet for the ready-treated product. The injector further displays an inlet for steam which is caused, under high pressure, to mingle, through various arrangements with gaps or ducts, with the product and heat it to the desired temperature. A conventional so-called annular gap injector is described in Swedish Patent Specification SE 367 121.

When it is the intention to treat viscous products, such as partly frozen juice concentrate, jams, ice cream mixes, sauces, creams and the like, it may be necessary to employ a different type of injector. One such injector is described, for example, in Swedish Patent Specification SE 517 823. In this type of injector, steam under high pressure enters into the product through a large number of ducts in the product pipe.

Heating by injection may occasionally give rise to sedimentation in the product, above all milk products. This is because of the combination of thermal effect and the mechanical effect which takes place when the steam bubbles entering into the product implode. Sedimentation in the product is entirely a matter of appearance and does not affect its flavour. In order to obviate such sedimentation, it is possible to homogenise the product under elevated pressure.

The distribution of the steam in the product may also constitute a problem as regards injection heating. Above all, this applies when the intention is to heat-treat viscous products, and then in particular in the employment of annular gap injectors. One method of addressing this problem is to employ and injector of the type which has a multiplicity of steam ducts in the product pipe. However, this type of injector has a shorter operative production time since the steam ducts are easily blocked by so-called fouling, in other words when the heated product burns onto the ducts.

A further problem in heating by means of an injector is that disturbing noise often occurs in the injector. The disturbing noise is so-called cavitation noise which occurs when the steam bubbles fed into the product implode. Today, there are no simple methods of obviating the problem of the high noise level.

OBJECTS OF THE INVENTION

One object of the present invention is to realise as device in an injector which counteracts the risk of sedimentation in the product.

A further object of the present invention is to realise a device in an injector which, in a simple and reliable manner, contributes in ensuring that steam is dissipated in the product.

Yet a further object of the present invention is that the device according to the invention considerably reduces the disturbing noise level which may occur in heat treatment by means of injection heating.

SOLUTION

These and other objects have been attained according to the present invention in that the method of the type described by way of introduction has been given the characterising feature that the pressure is raised immediately before the product leaves the injector.

These and other objects have also been attained according to the present invention in that the device of the type described by way of introduction has been given the characterising feature that a throttle washer is disposed immediately after the product outlet.

Preferred embodiments of the present invention have further been given the characterising features as set forth in the appended subclaims.

BRIEF DESCRIPTION OF THE ACCOMPANYING DRAWINGS

One preferred embodiment of the present invention will now be described in greater detail hereinbelow, with particular reference to the accompanying Drawings. In the accompanying Drawings.

The Drawings show only those details essential to an understanding of the present invention and the positioning of the injector in a heat-treatment plant—which is well-known to a person skilled in the art—has been omitted.

DESCRIPTION OF PREFERRED EMBODIMENT

Figure 1:
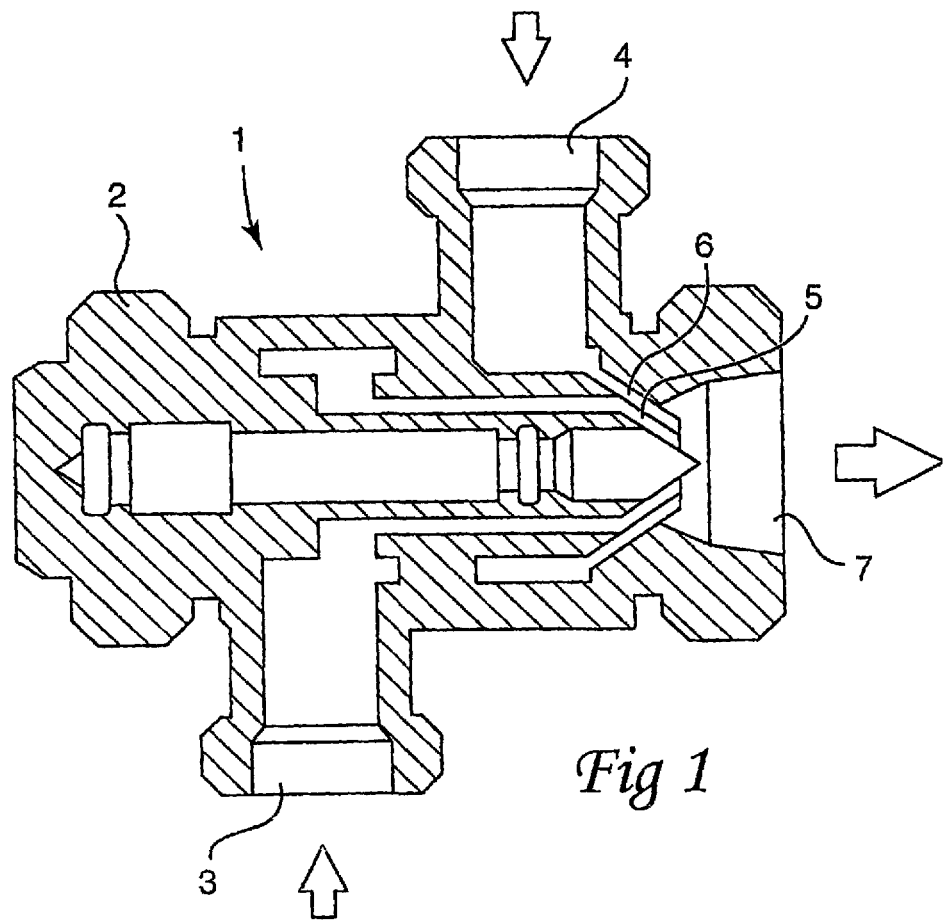
FIG. 1 is a schematic illustration of a so-called annular gap injector.
Figure 2:
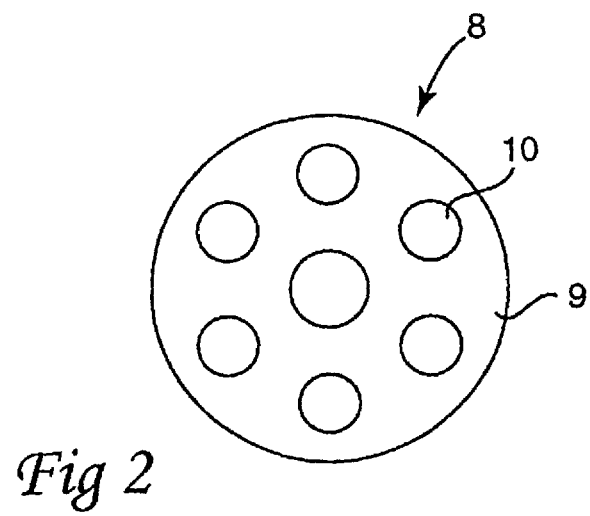
FIG. 2 shows a device according to the present invention.

FIG. 1 is a schematic illustration of an annular gap injector 1 in which a device according to the present invention may be employed. The device may be employed for all types of injectors.

The injector 1 has an injector housing 2 in which there is disposed an inlet 3 for product and an inlet 4 for steam. Through narrow annular gaps 5, 6, partly for product and partly for steam, steam and product are thus brought together. Both product and steam are pressurised. When the steam enters into the product, a very rapid heating of the product will be obtained. The product may consist of food products of various types and varying viscosities, such as dairy produce, juices, purees, creams and the like.

The heated product departs from the injector 1 through a product outlet 7 which is also disposed in the injector housing 2. After the injector 1, the product is conveyed further for continued processing or treatment in the plant.

When the steam enters the considerably colder product, there will, on the one hand, be obtained a condensation of the steam, and, on the other hand, an implosion of steam bubbles because of the pressure drop across the injector 1. The intention is to reduce the implosion as far as possible, since this may, on the one hand, give rise to sedimentation in the product and, on the other hand, give rise to disturbing noise.

By increasing the pressure across the injector, it is possible to reduce the risk of imploding steam bubbles in that increased pressure reduces the size of the steam bubbles. Small steam bubbles are not as likely to cause a mechanical processing of the product. Small steam bubbles also give improved distribution of the steam in the product, so that thermal stratification is avoided which otherwise easily occurs, above all in annular gap injectors 1. The pressure should be increased by 0.5-5 bar.

In order to increase the pressure across the injector 1, there is provided, in the device according to the present invention, a throttle washer 8 in immediate association with the product outlet 7 of the injector 1. The throttle washer 8 consists of a metal plate 9, preferably manufactured from stainless steel. Other materials which are food-approved and which withstand the washing to which the plant is subjected may also be used. The metal plate 9 is preferably of a thickness of 2-10 mm and it should have the same diameter as the outlet 7 of the injector 1.

The throttle washer 8 displays a number of through-going holes 10. Depending on the capacity of the injector 1 and the pressure elevation it is intended to achieve using the device, the number of holes 10 and their size may vary. The holes 10 are preferably uniformly distributed over the surface of the metal plate 9. The holes 10 together take up less than 50% of the surface 9 of the metal washer and preferably 10-30% of its surface.

The device according to the present invention may be employed for all types of injectors 1. When the pressure rises just before the product leaves the injector 1 and is forced through the throttle washer 8, the steam bubbles in the product will reduce in size and there will be a reduced risk of implosion. Once the product has passed the throttle washer 8, the pressure will once again fall and turbulence will occur which assists in distributing the steam bubbles in the product.

As will have been apparent from the foregoing description, the present invention realises a method and a device in an injector which, in a simple and economical manner, contribute in realising reduced sedimentation in the product, which imparts to the product a more attractive appearance. The method and the device also assist in distributing steam in the product more efficiently so that there will be obtained a more reliable heat treatment of the product. Finally, the method and the device according to the present invention contribute in considerably reducing the disturbing noise level which is a common occurrence in connection with the employment of injectors, so that the noise level becomes acceptable.

What is claimed is:

1. A method of improving steam distribution in an annular gap steam injector comprising:
    introducing product into a product inlet of a housing of the injector, the product inlet being in fluid communication with an annular product gap in the housing so that the product introduced into the product inlet flows into the annular product gap;
    introducing steam into a steam inlet of the housing, the steam inlet being in fluid communication with an annular steam gap in the housing so that the steam introduced into the steam inlet flows into the annular steam gap;
    bringing together the steam in the annular steam gap and the product in the annular product gap to heat the product;
    the heated product departing from the housing by way of an outlet; and
    increasing pressure across the injector to reduce a possibility of implosion of steam bubbles, the pressure across the injector being increased by conveying the heated product through a throttle washer positioned relative to the outlet to increase the pressure immediately before the heated product leaves the injector, the throttle washer comprising a plate provided with a plurality of through holes.

2. The method as claimed in claim 1, wherein the pressure is raised 0.5-5 bar.

3. The method as claimed in claim 1, wherein the product is a food product.

4. A steam injector for injecting steam into a product to heat the product, the steam injector comprising:
    a housing;
    an annular product gap inside the housing;
    a product inlet in fluid communication with the annular product gap and adapted to receive product so that the product introduced into the product inlet flows into the annular product gap;
    an annular steam gap inside the housing separate from the annular food gap and connected at one end to one end of the annular product gap;
    a steam inlet in fluid communication with the annular steam gap and adapted to receive steam so that the steam introduced into the steam inlet flows into the annular steam gap;
    an outlet;
    the one end of the annular product gap and the one end of the annular steam gap communicating with each other upstream of the outlet to bring together the product and the steam to heat the product; and
    a throttle washer positioned relative to the outlet to increase the pressure of the heated product immediately before the heated product leaves the injector to reduce a possibility of implosion of steam bubbles, the throttle washer comprising a plate provided with a plurality of through holes.

5. The steam injector as claimed in claim 4, wherein the holes in the plate take up less than 50% of the surface of the plate.

6. The steam injector as claimed in claim 4, wherein the holes in the plate take up 10 to 30% of the surface of the plate.

7. The steam injector as claimed in claim 4, wherein the throttle washer has a thickness of 2 to 10 mm.

8. The steam injector as claimed in claim 4, wherein the throttle washer is manufactured from stainless steel.

* * * * *

UNITED STATES PATENT AND TRADEMARK OFFICE
CERTIFICATE OF CORRECTION

PATENT NO.       : 7,637,484 B2
APPLICATION NO.  : 10/546735
DATED            : December 29, 2009
INVENTOR(S)      : Lopez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 867 days.

Signed and Sealed this

Ninth Day of November, 2010

David J. Kappos
*Director of the United States Patent and Trademark Office*